United States Patent [19]

Hoogendoorn et al.

[11] 4,439,049
[45] Mar. 27, 1984

[54] TEMPERATURE SCANNER

[75] Inventors: Bastiaan Hoogendoorn, Heemskerk; Nicolaas L. van Schagen, Alkmaar; Johannes C. A. van den Bemt, Schagen; Jan W. Zeijlmans, Santpoort-Noord, all of Netherlands

[73] Assignee: Estel Hoogovens B.V., Netherlands

[21] Appl. No.: 345,086

[22] Filed: Feb. 2, 1982

[30] Foreign Application Priority Data

Feb. 2, 1981 [EP] European Pat. Off. ........ 81200070.1

[51] Int. Cl.³ .......................... G01J 5/00; G01K 13/06
[52] U.S. Cl. ......................................... 374/124; 374/5; 374/137
[58] Field of Search ..................... 374/124, 129, 137, 5

[56] References Cited

U.S. PATENT DOCUMENTS 3,401,551 9/1968 Maley .
3,483,721 12/1969 Apple et al. .
3,736,375 5/1973 Parnet .
3,990,284 11/1976 Barten .
4,324,138 4/1982 Davis et al. .................... 374/137 X

FOREIGN PATENT DOCUMENTS 1473258 10/1969 Fed. Rep. of Germany .
2397627 7/1978 France .

OTHER PUBLICATIONS

Patent Abstracts of Japan, vol. 1, No. 92, Aug. 25, 1977, p. 2358 E 77 & JP-A 52 26268 (Nippon Denshi).
Control Engineering, vol. 11, No. 5, May 1964, S. Sorsen: "17 Ways to Track the Edge", pp. 77–80.
Iron Age, vol. 193, No. 14, Apr. 2, 1964, "Gage Reads Width of Hot Strip", p. 61.
Electronique Industrielle, vol. 113, May 1968, P. Conjeaud et al., "Le Thermographe Infrarouge", pp. 309–314.

Primary Examiner—Gerald Goldberg
Assistant Examiner—Joseph W. Roskos
Attorney, Agent, or Firm—Stevens, Davis, Miller & Mosher

[57] ABSTRACT

A temperature scanner for use in a hot strip rolling mill to enable ready determination and analysis of the temperature distribution over a hot strip of material passing through the mill. The temperature scanner comprises a photocell scanner unit 1, situated over and scanning a strip 2 perpendicular to its direction of travel, electronic analyzer 6 connected to the scanner unit via lead 5 and displayer 7 connected to the analyzer 6 by lead 8. The analyzer 6 compares the temperatures detected with a reference level set and together with the displayer 7 displays a map of the strip surface in which areas at temperature above the reference level are distinguished from those below the reference level. Alternatively, one or more temperature profiles corresponding to one or more scans of the surface are displayed, in which temperatures above the reference level are distinguished from those below the reference level.

7 Claims, 9 Drawing Figures

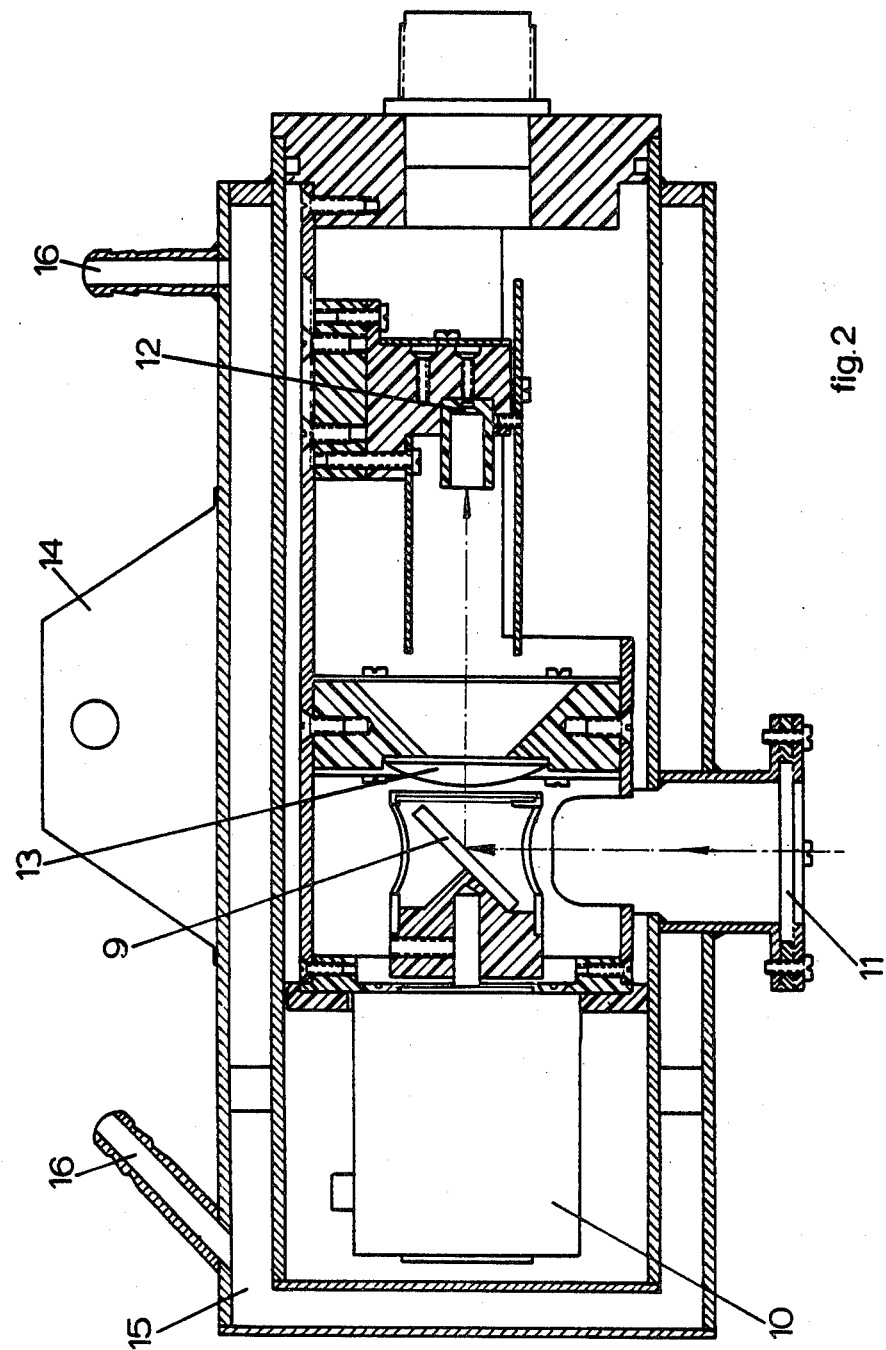

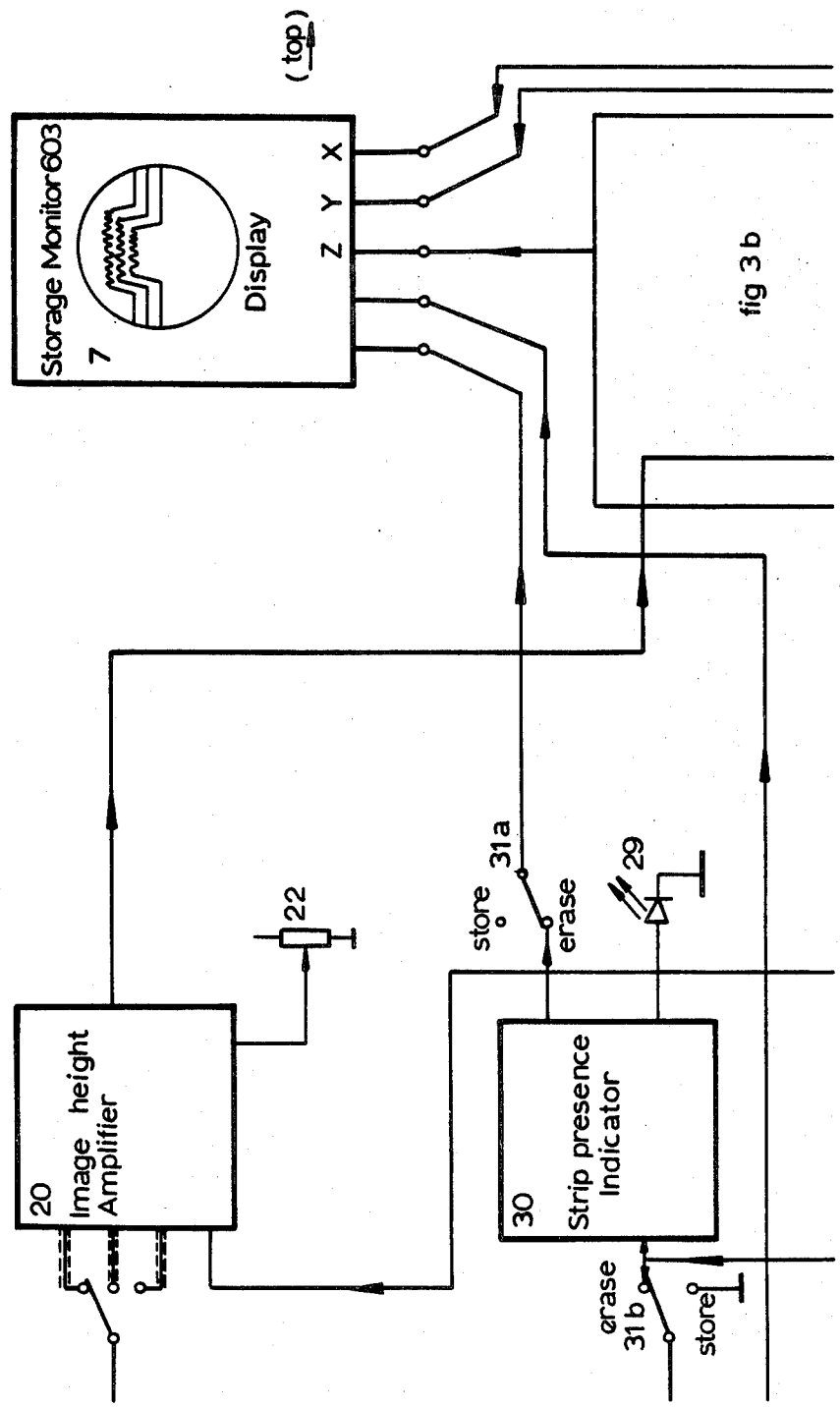

TEMPERATURE SCANNER

BACKGROUND OF THE INVENTION

1. Field of the Invention

This invention relates to a temperature scanner for detecting the temperatures or relative temperatures of positions on the surface of a hot steel strip moving relative to said scanner and in particular to analysis and display means used in such a scanner.

2. Description of the Prior Art

Temperature scanners of this kind have many applications but are particularly useful in steel rolling mills. In a hot steel strip rolling mill for example a hot steel strip is progressively lengthened and reduced in thickness by being passed through a train of rolling stands. The hotter the steel is, the more ductile it becomes. This however, leads to the disadvantage that an uneven temperature distribution over the strip will result in some portions being lengthened and reduced in thickness to a greater extent than other portions. In a rolling mill where high speeds are achieved by the strip as a result of its being lengthened, such uneven elongation can result in dangerous buckling or deviation of the strip from its intended path. Even if the uneven treatment is not sufficient to cause an accident the quality of the strip will be adversely affected by damage to the strip edges, caused by the strip scraping against stops on the strip table.

It is therefore very desirable to have a readily accessible and understandable means of assessing the temperature distribution over a strip passing through such a mill so that action may be taken to prevent any unevenness in the temperature distribution. It would also be desirable to have a ready means of continuously determining whether such a strip was correctly aligned in the mill and to be able to continuously measure the strip width during rolling.

Various infra-red temperature scanners have been proposed in the past. FR 2397627 discloses an infra-red pyrometer and mirror for scanning the temperature of the output of a sintering plant. The information desired is displayed solely as temperature profiles. The device disclosed is first of all unsuitable for use in a hot steel strip rolling mill for several reasons. A sintering line has a very low speed in contrast to a hot strip mill, the device is not suitable for accurately measuring temperatures between 800° and 1000° C. as encountered in a hot strip mill and furthermore the device cannot determine the temperature of a fast moving hot steel strip having an emission coefficient of 0.8. In addition a sintering line is confined by vertical walls and the device is incapable of determining the width of a steel strip. Secondly and more importantly the display of the information collected by the infra-red scanner can only be present as temperature profiles which thus severely limits the ease of comprehension and choice as to the most convenient form of presentation for the operator.

U.S. Pat. No. 3,736,375 again uses infra-red pyrometry but in this case uses it to study a ribbon of glass. This too is relatively slow moving and again only enables one form of presentation to be used. This is in the form of a temperature contour chart incorporating a reference contour and a median contour. However the device is unsuitable for use with a hot steel strip rolling mill in which the steel strip moves considerably faster. Furthermore the lack of choice concerning the display mode again severely limits the case of comprehension and choice as to the most convenient form of presentation for the operator.

In the past the use of infra red sensors has been proposed to monitor the temperature of a steel strip (DT-AS 2349611). However the information derived by such sensors has been used directly to control the rolling stands, and no readily accessible and understandable means of analysing the output obtained by such a sensor and making it directly available to an operator has been proposed.

OBJECT OF THE INVENTION

The object of the present invention is to provide a scanner, specifically for hot steel strip, which provides useful displayed information for operators and for quality control.

SUMMARY OF THE INVENTION

The scanner of the invention provides three possible modes of display, any one of which may be selected. In the first a map of the hot surface is displayed, which enables easy overall monitoring of the condition of the surface, e.g. a hot rolled strip. The map may show the whole surface or may be made up from a large number of spaced apart scanned areas of the surface. This map may be a "black/white" display, black for areas below a given threshold temperature and white for areas above the given temperature (or vice versa). Preferably the data used to provide the map display can be reprocessed with respect to a different threshold temperature, to provide a different map. In the second mode it displays simultaneously temperature profiles of a plurality of different scanned areas. In the third mode there is a continuous display of the temperature profile of the area last scanned.

In all display modes, parts of the display representing temperatures above a given reference level may be distinguished from those below the reference level.

The device thus advantageously provides a readily visible, accessible and understandable means of assessing the temperature distribution over the scanned surface. The device also has the advantage that it is possible to observe the temperature distribution of an entire strip after it has passed through the mill and that it is also possible to study the temperature profile of the strip as it passes the scanner. The present invention also has the advantage that it is able to act as an edge detector for the strip and it is thus capable of determining the width of the strip and whether the strip is keeping to its preferred path. This is a result of the temperature of the strip being higher than that of its surroundings.

BRIEF DESCRIPTION OF THE DRAWINGS

A preferred embodiment of the present invention is described below with reference to the accompanying drawing in which:

FIG. 2 is a cross sectional view of the scanning means shown in FIG. 1.

DESCRIPTION OF THE PREFERRED EMBODIMENTS

Figure 1:
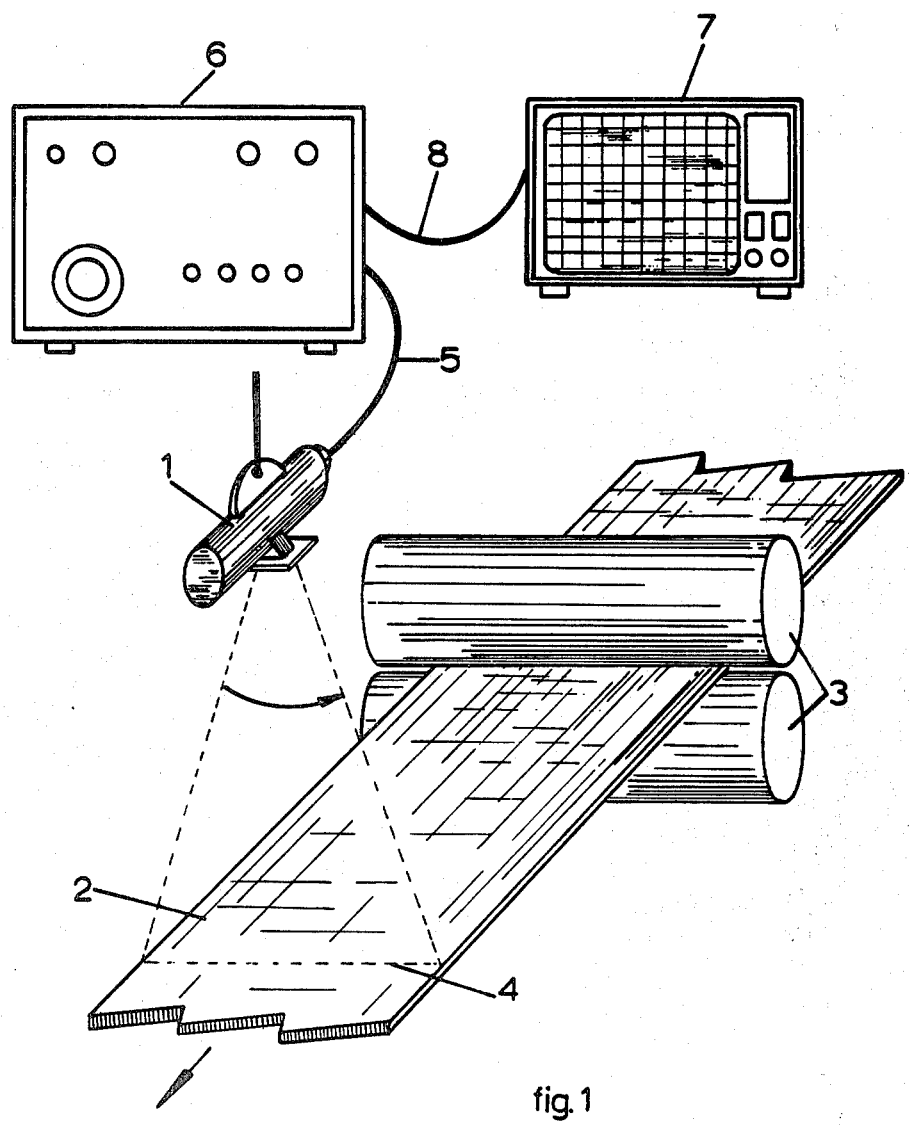
FIG. 1 shows analysis and display means associated with a photocell and scanning means arranged above a strip being passed through a pair of rollers.

In FIG. 1 a photocell and associated scanning means 1 are shown mounted above a hot strip 2 being passed between rollers 3. In each scan the photocell and scanning means 1 observes the area of the strip indicated by the dashed lines 4 which is perpendicular to the direction in which it passes underneath the photocell and scanning means. The output from the photocell 1 is then passed via connecting lead 5 to electronic analysis means 6. The output from the electronic analysis means 6 is then passed to display means 7 via connecting lead 8. The display means 7 comprises a storage monitor (e.g. one made by Tektronix, model No. 603A).

The photocell and associated scanning means 1 are shown in greater detail in FIG. 2. A gold coated mirror 9 is rotated by a motor 10 and reflects radiation passing through a pyrex observation port 11 onto a germanium photocell 12 via a pyrex condensing lens 13. The mirror 9 is rotated with its axis parallel to the direction of travel of the surface being observed and scans an angle of 60° through the port 11. The minimum angle which the strip should subtend at the mirror is 4°.

The photocell and scanner unit is suspended above the strip using mounting lug 14. As the unit is preferably only 1 to 2 times the width of the strip above the strip (often only about 2.5 m) where it may be extremely hot, the unit is provided with a liquid cooling jacket 15 with inlet and outlets 16. The photocell used is preferably one with a low sensitivity to both visible light and the wavelength at which IR absorption by vapor occurs. The photocell is provided with an infra red filter and is sensitive over the range 0.8–0.2 um with a maximum sensitivity at 1.55 um. The photocell thus has a high sensitivity for radiation emitted by the hot strip but a low sensitivity to the effects of water vapour and variations in the emission coefficient of the strip. In a rolling mill, there is likely to be much water vapour in the atmosphere.

The surface area observed at any one instant is approximately 18 mm in diameter and as the scanning frequency is 25 $s^{-1}$ the photocell is able to scan a series of substantially parallel strips on the strip surface. Scanning occurs during about 6.7 mS of the 40 mS that each rotation of the mirror lasts and the photocell produces a voltage of 6.206 volts via a built-in preamplifier when receiving radiation from a black body at 1100° C.

As shown in FIG. 1 the output from the photocell and scanner unit is passed to the electronic analysis means 6 via lead 5. The photocell and scanner unit is arranged so that a 0.5 mS trigger pulse is also sent to the analysis means 6 along lead 5, 6° or 0.7 mS before the mirror 9 starts to scan through the aperture 11.

Figure 3A:
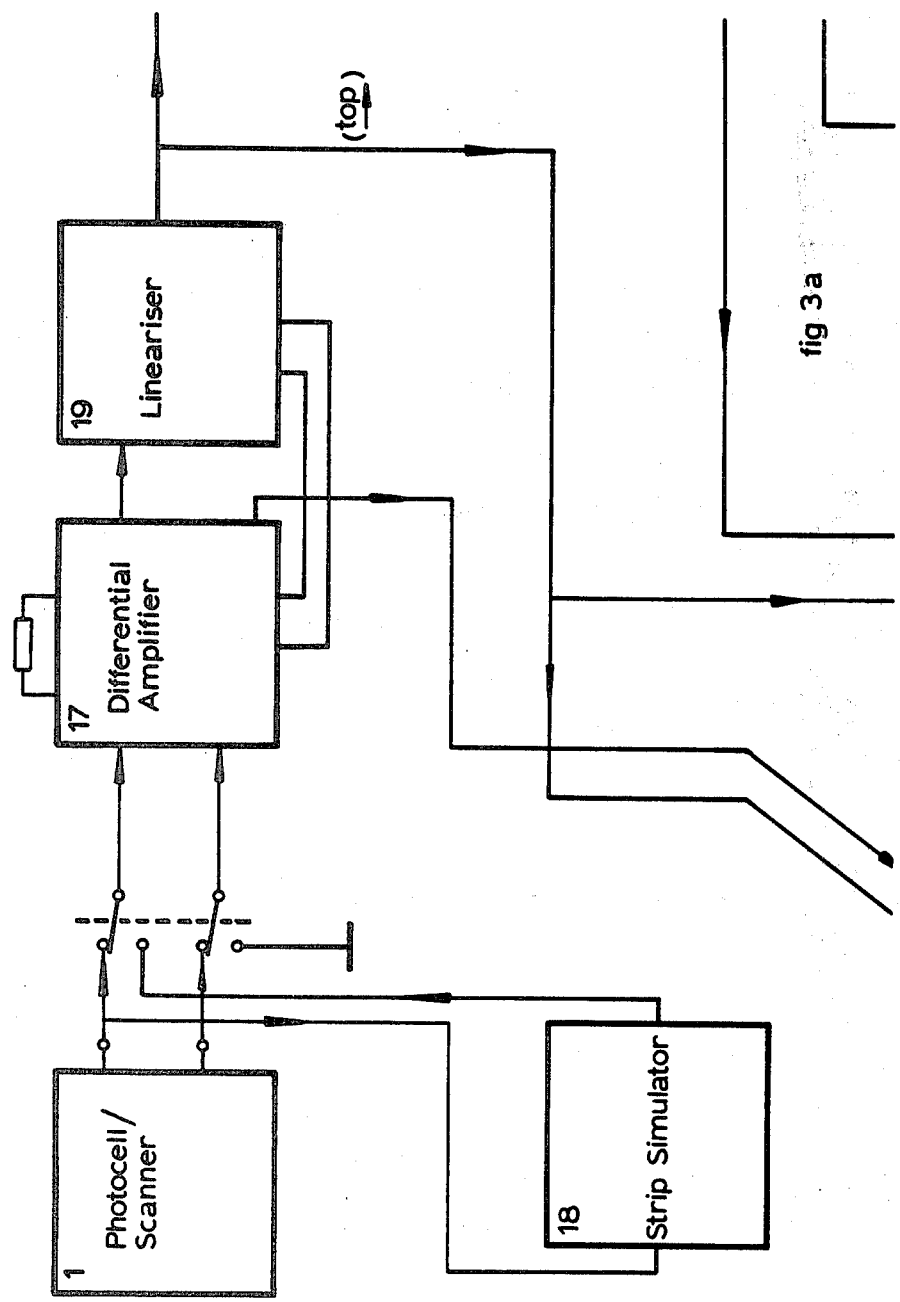
FIG. 3 is a block diagram of the electronic analysis means.
Figure 3C:
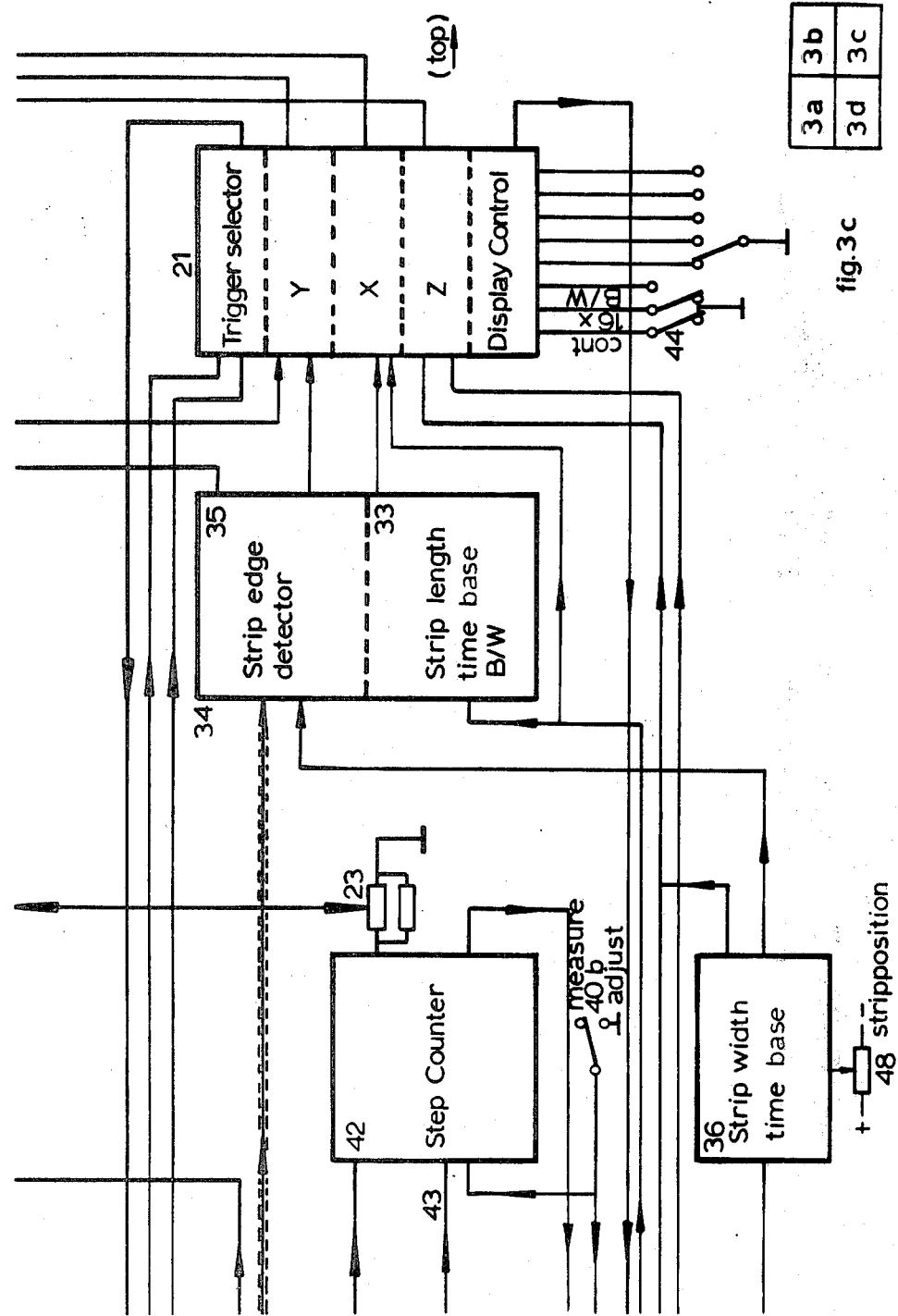
Figure 3D:
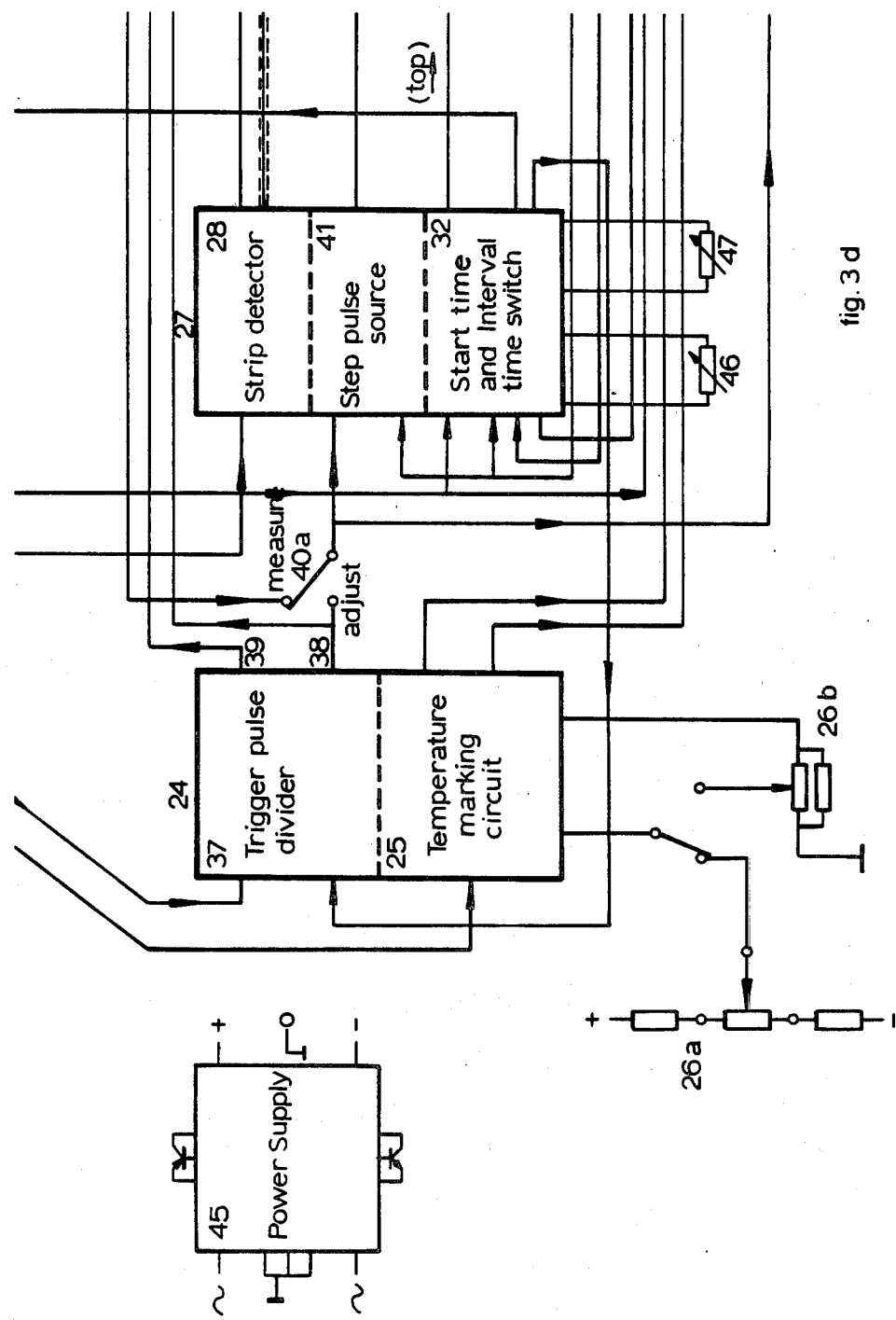

As shown in FIG. 3 this signal and a zero level signal are passed to a circuit 17 comprising a differential amplifier. Random voltages induced in the lead 5 are thus eliminated. A strip simulator circuit 18 may be switched into the circuit instead of the photocell and scanner output in order to test the device. The strip simulator circuit 18 produces a synthesized temperature signal every 40 mS using an oscillator and amplitude compression circuit. In the circuit 17 after the differential amplifier the temperature signal and the trigger signal are separated. The temperature signal is sent to the lineariser circuit 19 via an emission coefficent resistor and is amplified in the lineariser circuit 19 by a factor of 1.25 (that being the reciprocal of the emission coefficient of steel). The lineariser circuit 19 converts the signal to a linear temperature signal of 10 mV per °C. for temperatures above 500° C. The temperature signal then passes to the image height amplifier circuit 20 via a switch which selects a scale of 0.1 volt per 20,50 or 100 cm for temperatures above 500° C. when the "16 line" or "continuous" display mode is used. The temperature signal is then transmitted to the Y input of the display means 7 via a switching system 21. The zero level may be adjusted by potentiometer 22 and the step height by potentiometer 23. The temperature signal is also fed to the circuit 24 which contains the temperature marking circuit 25. This circuit 25 compares the input temperature signal with a reference level set by either of potentiometers 26a or 26b. If the signal indicates a temperature lower than that corresponding to the reference level the signal is fed to the Z or brightness input of the display means via switching circuit 21 and a multivibrator which suppresses the signal 20,000 times a second thus creating a dotted line. If the temperature is above the reference level the signal is fed directly to the switching circuit 21 thus forming a continuous line. When the "black/white" display mode is selected the comparator will completely suppress the Z input signal when the temperature signal is below the reference level.

The temperature signal from the lineariser 19 is also fed to the circuit 27 which contains the strip detector circuit 28. This, via a delay to prevent premature operation between scans or when cold areas of the strip are detected, indicates that a strip is present using an LED 29 via circuit 30 and also permanently switches the erase switch on the display means 7 on, as long as a strip is present and the switch 31 is set to erase. The monitor screen will thus be erased when a new strip appears and cannot be erased in between by pressing the erase switch on the display.

The strip detector circuit 28 also, via switch 31b, switches on the start time switch circuit 32 which is also in circuit 27. The strip detector circuit 28 also switches on the strip length time base circuit 33 which forms part of circuit 34. The strip length time base circuit 33 provides the X input to the display during the use of the "black/white" display mode.

The strip detector 28 also provides a strip width voltage signal which is used to indicate the width of the strip. The strip edges are determined by taking the temperature at any instant which is midway between the peak value and 500° C. to represent the position of the strip edges. The strip width signal is fed to the strip edge detector circuit 35 which forms another part of circuit 34. The strip edge detector circuit 35 provides a short positive pulse at the Z input of the monitor so that lines representing the strip edges are displayed during the black/white display mode. This pulse appears after the detection of the edge and to compensate for this delay the Y time base voltage from the strip width time base circuit 36 is also delayed.

The trigger signals from the differential amplifier 17 are transmitted by the trigger pulse divider circuit 37 in circuit 24 only if they exceed 7 volts. In this way extraneous pulses below 7 volts may be eliminated. At a first output 38 of the divider circuit 37 all trigger pulses are emitted. At the second output 39 only pulses which start with the arrival of those pulses arriving immediately after the end of the start or interval time are emitted. The start time is the length of time between the detection of the strip and the display of the first temperature profile and the interval time is the time between the display of successive profiles in the case of the "16 line" display mode. The signals from the outputs 38 and 39 then travel via the tigger control circuit of circuit 21 to switch 40a (which may be set to "adjust" or "measure" positions) and thence to the step pulse source circuit 41 in circuit 27 and to the strip width time base circuit 36 when the switch 40a is in the "measure" position. When the switch 40a is in the "adjust" position, the output from the first output 38 alone is fed directly to the step pulse circuit 41 and to the strip width time base circuit 36.

The step pulse source circuit 41 passes incoming pulses to the step counter circuit 42 as long as this does not block such signals by sending the step pulse source circuit a stop measuring signal. The step counter circuit 42 counts a plurality of steps down during the display of a plurality of temperature profiles. In this example 16 are counted (hence "16 line" display mode). If the strip passes earlier the counter will stop. The stepcounter will be reset and stopped if the reset entry input 43 is at a low voltage, for example after the temperature signal ceases and if switch 44 is set to the "continuous" display mode position. The stepcounter also operated during the black/white display mode, in this case the resulting image height is not passed to the display. When switching over from "black/white" display mode to the "16 line" display mode the stepcounter is reset as the switch 44 is a "break before make" switch.

The start and interval time switch circuit 32 comprises three monostable flipflops. These are each associated with either the start time, an auxiliary time (0.8 s) or the interval time. The "auxiliary time" and "interval time" flip flops form a circuit which is switched on by the start time flip flop. The "auxiliary time" flip flop switches on an AND gate in circuit 24 so that the next trigger edge is passed to output 39. The circuit 27 also blocks the "store" function of the display during the "continuous" display mode and when switch 40 is set to "adjust".

The switching system circuit 21 connects the X,Y and Z display inputs to the correct outputs and selects the correct trigger pulses for the "16 line" or "black/white" display modes.

The time base for the strip width is fed to the X input in the "continuous" and "16 line" display modes and to the Y input via an amplifier having an amplification factor of 0.8 during the "black/white" display mode.

The power supply circuit 45 receives 2×18 volts and the output voltage is ±15 v. The power transistors are mounted on the mounting plate of the box containing the analysis means.

Figure 4:
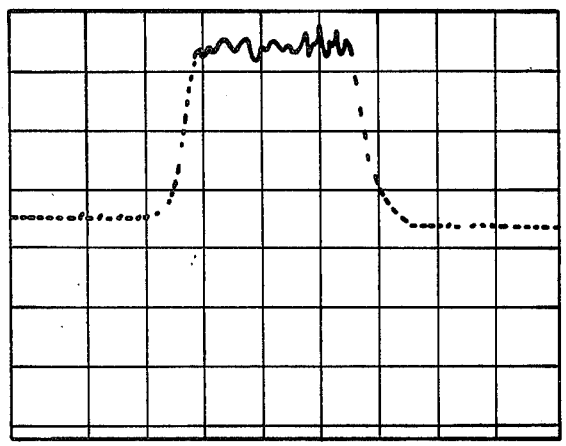
FIGS. 4, 5 and 6 show representations of three different display modes as they appear on the display means.

The operator of this embodiment of the present invention thus has a choice of three display modes, to each of which he may make a number of adjustments. On selecting the continuous display using switch 44 the operator will observe a temperature profile of the strip which is continuously updated as the strip passes the detector. The operation may select either of potentiometers 26a or 26b, one of which may be a preset one within the analysis means and the other of which may be manually adjustable by the operator, and then he may set either to determine a reference temperature below which the temperature profile on the screen will appear as a dotted line as shown in FIG. 4.

Figure 5:
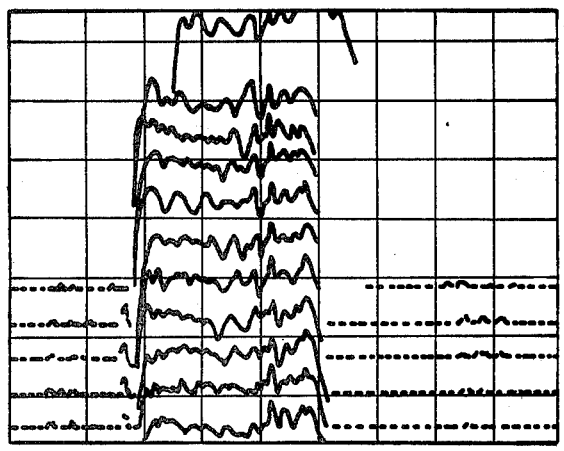

When the operator selects the "16 line" display mode a certain time (the start time which is adjustable using a variable resistor 46) will elapse from the moment the strip is detected and a temperature profile of the strip will then be displayed. After another time interval (the interval time which is adjustable using variable resistor 47) another line will be displayed, below the first, corresponding to another temperature profile. This process will continue until sixteen temperature profiles are displayed on the screen, in the manner shown in FIG. 5, or until the strip is no longer detected by the scanner. The spacing between the lines may be adjusted using the step level control 23. If the switch 40 is set to "adjust", the sixteen temperature profiles will appear in quick succession so that the display can be adjusted. If the switch 31 is set to "erase", the display will be erased and a new reading started whenever a new strip passes the scanner. When set to "store" the display just recorded will be retained so that it can be photographed or studied.

The switch 31 performs a similar function during the black/white display mode. The temperature profiles displayed during the "16 line" display mode will also appear as dotted lines when below the set reference temperature as in the continuous display.

Figure 6:
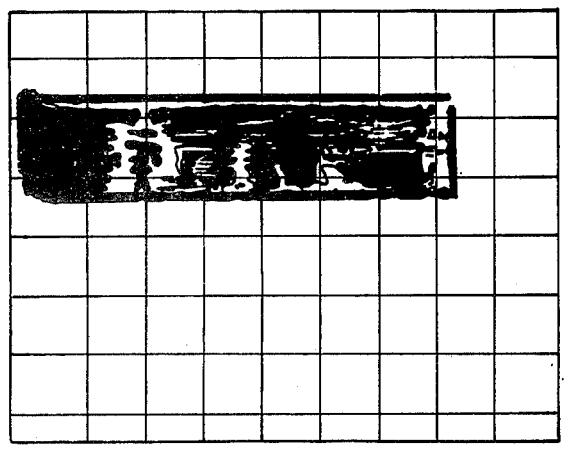

When the "black/white" display mode is selected two horizontal lines appear on the screen indicating the location of the strip edges and a black and white temperature map of the entire strip will be built up as shown in FIG. 6. Those areas above the reference temperature will be shown in white and those below in black.

The strip position on the display may be adjusted using potentiometer 48. This will move the display in the X direction during the "continuous" and "16 line" display modes and in the Y direction during the "black/white" display mode.

What is claimed is:

1. A temperature scanner for scanning the temperature of the surface of a hot steel strip moving relative to the scanner, the scanner comprising
   (a) a photocell,
   (b) scanning means enabling said photocell to optically scan a plurality of different strips across said surface as the surface moves,
   (c) electronic analysis means connected to said photocell, and
   (d) display means connected to said electronic analysis means to display the output of said electronic analysis means,
   (e) said electronic analysis means is adapted to operate in all of three modes, which modes are
      (i) a first mode in which said electronic analysis means compares the temperatures detected by said photocell with a reference temperature level and through said display means displays a map of the surface in which areas of the surface whose temperatures are above said reference temperature level are distinguished from areas whose temperatures are below said level,
      (ii) a second mode in which at least one temperature profile across the surface obtained from one or more scans of said surface strips is displayed, and
      (iii) third mode in which a plurality of said profiles are displayed simultaneously, spaced apart on the display means,
   (f) said electronic analysis means further comprising switching means enabling operation of said electronic analysis means in any one of the said three modes of operation.

2. A scanner according to claim 1 wherein in said second and third modes portions of any of said temperature profile or profiles above said given reference temperature level are distinguished from portions below said level.

3. A scanner according to claim 1 adapted to detect the difference in temperature between said surface and its surroundings so as to provide a display of an edge of said surface.

4. A scanner according to claim 1 adapted to determine the width of said surface.

5. A scanner according to claim 1 wherein in said first mode said reference temperature level is adjustable.

6. A scanner according to claim 1 wherein in said second and third modes portions of any of said temperature profile or profiles above a given adjustable reference temperature level are distinguished from portions below said level.

7. A scanner according to claim 1 wherein said display means comprises a unit which both continuously stores output from said analysis means and continuously displays said stored output.

* * * * *